(12) United States Patent
Simpkins

(10) Patent No.: US 8,063,020 B2
(45) Date of Patent: *Nov. 22, 2011

(54) RESUSCITATION FLUID

(76) Inventor: Cuthbert O. Simpkins, Shreveport, LA (US)

( * ) Notice: Subject to any disclaimer, the term of this patent is extended or adjusted under 35 U.S.C. 154(b) by 334 days.

This patent is subject to a terminal disclaimer.

(21) Appl. No.: 12/314,737

(22) Filed: Dec. 16, 2008

(65) Prior Publication Data

US 2009/0163418 A1 Jun. 25, 2009

Related U.S. Application Data

(60) Provisional application No. 61/016,443, filed on Dec. 22, 2007, provisional application No. 61/064,639, filed on Mar. 18, 2008.

(51) Int. Cl.
*A61K 38/00* (2006.01)
*A61P 7/00* (2006.01)

(52) U.S. Cl. ............ 514/13.4; 514/13.5; 514/15.2; 424/283.1

(58) Field of Classification Search ............ 514/12, 514/13.4, 13.5, 15.2; 424/283.1
See application file for complete search history.

(56) References Cited

U.S. PATENT DOCUMENTS

| | | | |
|---|---|---|---|
| 4,182,750 | A | 1/1980 | Sullivan et al. |
| 4,425,334 | A | 1/1984 | Hunt |
| 4,911,929 | A | 3/1990 | Farmer et al. |
| 5,284,663 | A | 2/1994 | Speaker |
| 5,576,016 | A | 11/1996 | Amselem et al. |
| 5,635,207 | A * | 6/1997 | Grinstaff et al. ............ 424/450 |
| 6,261,537 | B1 | 7/2001 | Klaveness et al. |
| 7,105,151 | B2 | 9/2006 | Unger et al. |
| 7,417,118 | B2 | 8/2008 | Kai et al. |
| 2001/0028893 | A1 | 10/2001 | Spears |
| 2002/0172710 | A1 | 11/2002 | Twine |
| 2003/0113351 | A1 | 6/2003 | Fischer et al. |
| 2005/0260189 | A1 | 11/2005 | Klibanov et al. |
| 2006/0088583 | A1 | 4/2006 | Takeoka et al. |
| 2006/0166182 | A1 | 7/2006 | Weinberg et al. |
| 2009/0163418 | A1 | 6/2009 | Simpkins |
| 2009/0191244 | A1 | 7/2009 | Kheir et al. |
| 2010/0196461 | A1 | 8/2010 | Simpkins |

FOREIGN PATENT DOCUMENTS

| | | |
|---|---|---|
| WO | WO 03/009828 | 2/2003 |
| WO | WO 2004/060147 | 7/2004 |
| WO | WO 2009/082449 | 7/2009 |

OTHER PUBLICATIONS

U.S. Appl. No. 12/696,107.*
U.S. Appl. No. 60/975,705, filed Sep. 27, 2007, Kheir, et al.
U.S. Appl. No. 61/026,984, filed Feb. 7, 2008, Kheir, et al.
International Search Report issued Jan. 20, 2011in counterpart foreign application under the WIPO, Application No. PCT/US2010/000262.
Supplemental European Search Report issued Jan. 28, 2011in counterpart foreign application under the WIPO, Application No. PCT/US2008/013781.
Yun Suk Jo, et al.; Micelles for Delivery of Nitric Oxide; JACS Articles; J. AM. Chem. Soc.; 2009; 131; pp. 14413-14418.
Evan C. Unger, et al.; Therapeutic applications of lipid-coated microbubbles; Advanced Drug Delivery Reviews 56; 2004; pp. 1291-1314.
Meg A. Rosenblatt, et al.; Successful Use of a 20% Lipid Emulsion to Resuscitate a Patient after a Presumed . . . ; Anesthesiology; vol. 105, No. 1; Jul. 2006; pp. 217-221.
J. Eckart, et al.; Aktueller Stand der Parenteralen Ernahrung mit Fettemulsionen; Infusionstherapic 10; 1983; pp. 172-182.
G. Foxall, et al.; Levobupibacine-inducted seizures and cardiovascular collapse treated with Intralipid; The Ass. of Anaethesia . . . ; 62; 2007; pp. 516-518.
Susan Lanza-Jacoby, PHD, et al.; Parenteral Supplementation With a Fish-Oil emulsion Prolongs Survival and Improves Rat Lymphocyte . . . ; Nutrition; 17; 2001; pp. 112-116.
R. J. Litz, et al.; Successful resuscitation of a patient with ropivacaine-induced asystole after axillary plexus block . . . ; The Ass. of Anaesthesia; 2006; 61; pp. 800-801.
International Search Report issued Aug. 7, 2009 in counterpart foreign application under the WIPO, Application No. PCT/US2008/013781.
Robert J. Przybelski, M.D., et al.; Advances in Blood Substitutes; Industrial Opportunities and Medical Challenges; Chapter 5; pp. 71-85.
Cuthbert O. Simpkins, et al.; Histidine Inhibits the Degradation of Cells Suspended in Ringer's Lactate; The Journal of Trauma; 2007; pp. 565-572.

* cited by examiner

*Primary Examiner* — Ruth Davis
(74) *Attorney, Agent, or Firm* — Michael Ye; Andrews Kurth LLP

(57) ABSTRACT

A method for treating conditions related to lack of blood supply with a lipid based resuscitation fluid is disclosed. The resuscitation fluid contains a lipid component and an aqueous carrier. The lipid component forms an emulsion with the aqueous carrier. The resuscitation fluid can be used to increase the blood pressure and to carry oxygen to tissues. The resuscitation fluid can also be used for preserving the biological integrity of donor organs for transplantation.

17 Claims, 3 Drawing Sheets

RESUSCITATION FLUID

CROSS-REFERENCE TO RELATED APPLICATIONS

This application claims priority of U.S. Provisional Application Ser. No. 61/016,443, filed Dec. 22, 2007 and U.S. Provisional Application Ser. No. 61/064,639, filed Mar. 18, 2008, both of which are incorporated by reference in their entirety.

TECHNICAL FIELD

The technical field is medical treatment and, in particular, methods and compositions for treating conditions related to lack of blood supply.

BACKGROUND

When a large amount of blood is lost, it is critical to immediately replace the lost volume with a volume expander to maintain circulatory volume, so that the remaining red blood cells can still oxygenate body tissue. In extreme cases, an infusion of real blood or blood substitute may be needed to maintain adequate tissue oxygenation in the affected individual. A blood substitute differs from a simple volume expander in that the blood substitute has the ability to carry oxygen like real blood.

Currently employed blood substitutes use either perfluorocarbons (PFCs) or hemoglobins as the oxygen carrier. PFCs are compounds derived from hydrocarbons by replacing the hydrogen atoms in the hydrocarbons with fluorine atoms. PFCs are capable of dissolving relatively high concentrations of oxygen. However, medical applications require high purity perfluorocarbons. Impurities with nitrogen bonds can be highly toxic. Hydrogen-containing compounds (which can release hydrogen fluoride) and unsaturated compounds must also be excluded. The purification process is complex and costly.

Hemoglobin is the iron-containing oxygen-transport metalloprotein in the red blood cells. Pure hemoglobin separated from red blood cells, however, cannot be used since it causes renal toxicity. Various modifications, such as cross-linking, polymerization, ad encapsulation, are needed to convert hemoglobin into a useful and safe artificial oxygen carrier. The resulting products, often referred to as HBOCs (Hemoglobin Based Oxygen Carriers), are expensive and have a relative short shelf-life.

Therefore, there still exists a need for a lower-cost resuscitation fluid that functions as a volume expander but is also capable of carrying a large amount of oxygen.

SUMMARY

A method for treating conditions related to lack of blood supply is disclosed. The method includes administering to a subject in need of such treatment an effective amount of a lipid based resuscitation fluid that contains a lipid component and an aqueous carrier. The lipid component forms an emulsion with the aqueous carrier.

Also disclosed is a method for preserving the biological integrity of an organ of a mammalian donor organism. The method includes perfusing the organ with an effective amount of a lipid based resuscitation fluid containing a lipid component and an aqueous carrier, wherein the lipid component forms an emulsion with the aqueous carrier.

Also disclosed is a lipid based resuscitation fluid. The resuscitation fluid contains an oxygenated lipid emulsion and a buffering agent.

Also disclosed is a resuscitation kit. The resuscitation kit contains a lipid based resuscitation fluid having a lipid component and an aqueous carrier and an oxygenation device.

DESCRIPTION OF THE DRAWINGS

The detailed description will refer to the following drawings, wherein like numerals refer to like elements, and wherein.

DETAILED DESCRIPTION

Figure 1:
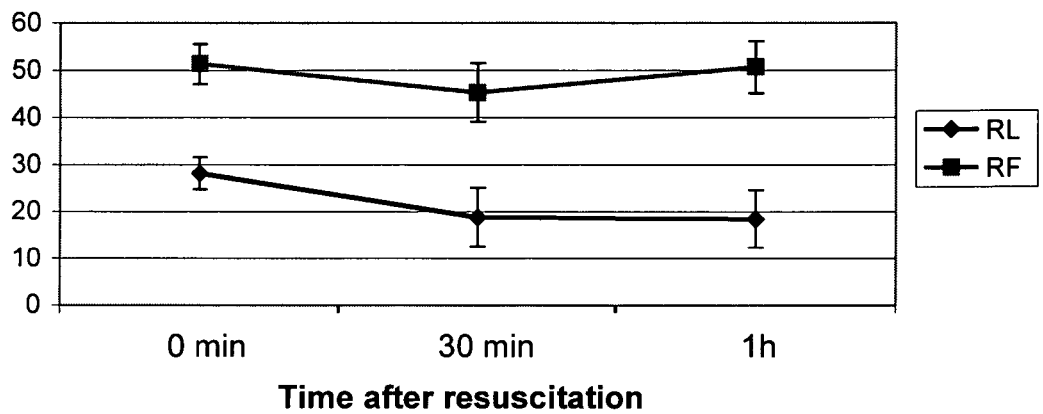
FIG. 1 is a diagram showing systolic blood pressure in mice treated with different resuscitation fluids after severe hemorrhagic shock.

One aspect of the present invention relates to a resuscitation fluid composition for treating conditions related to lack of blood supply with a lipid based resuscitation fluid. The resuscitation fluid comprises a lipid component and a polar liquid carrier. The lipid component is dispersed in the polar liquid carrier to form an emulsion that typically contains lipid micelles with a polar outer surface and an inner hydrophobic space. The resuscitation fluid can be used to increase blood pressure and to carry oxygen to tissues.

Lipid Component

The lipid component can be any lipid that is capable of forming an emulsion with water. As used herein, the term "lipid" refers to any suitable material resulting in a monolayer or lipid micelle in an aqueous environment such that a hydrophobic portion of the lipid material orients toward the inner portion of the lipid micelle while a hydrophilic portion orients toward the aqueous phase. Hydrophilic characteristics derive from the presence of phosphato, carboxylic, sulfato, amino, sulfhydryl, nitro, and other like groups. Hydrophobicity is conferred by the inclusion of groups that include, but are not limited to, long chain saturated and unsaturated aliphatic hydrocarbon groups, with such groups being optionally substituted by one or more aromatic, cycloaliphatic or heterocyclic group(s).

Examples of lipids include but are not limited to, fatty acyls, glycerolipids, phospholipids such as phosphatidylcholine (PC), phosphatidylethanolamine (PE), phosphatidic acid (PA), phosphatidylglycerol (PG), sphingolipids, sterol lipids such as cholesterol, prenol lipids, saccharolipids, polyketides, nonnatural lipid(s), cationic lipid(s) and mixtures thereof. In one embodiment, the lipid is a mixture of soybean oil and egg yolk phospholipids, such as those used in Intralipid® (marketed and sold by Baxter International Inc., Deerfield, Ill.).

Polar Liquid Carrier

The polar liquid carrier can be any pharmaceutically acceptable polar liquid that is capable of forming an emulsion with the lipid. The term "pharmaceutically acceptable" refers to molecular entities and compositions that are of sufficient purity and quality for use in the formulation of a composition or medicament of the present invention and that, when appropriately administered to an animal or a human, do not produce an adverse, allergic or other untoward reaction. Since both human use (clinical and over-the-counter) and veterinary use are equally included within the scope of the present invention, a pharmaceutically acceptable formulation would include a composition or medicament for either human or veterinary use. In one embodiment, the polar liquid carrier is water or a water based solution. In another embodiment, the polar liquid carrier is a non-aqueous polar liquid such as dimethyl sulfoxide, polyethylene glycol and polar silicone liquids.

A water-based solution generally comprises a physiologically compatible electrolyte vehicle isosmotic with whole blood. The carrier can be, for example, physiological saline, a saline-glucose mixture, Ringer's solution, lactated Ringer's solution, Locke-Ringer's solution, Krebs-Ringer's solution, Hartmann's balanced saline, heparinized sodium citrate-citric acid-dextrose solution, and polymeric plasma substitutes, such as polyethylene oxide, polyvinyl pyrrolidone, polyvinyl alcohol and ethylene oxide-propylene glycol condensates. The resuscitation fluid may additionally comprise other constituents such as pharmaceutically-acceptable carriers, diluents, fillers and salts, the selection of which depends on the dosage form utilized, the condition being treated, the particular purpose to be achieved according to the determination of the ordinarily skilled artisan in the field and the properties of such additives.

Plasma Component

The resuscitation fluid may further comprise a plasma component. In one embodiment, the plasma is an animal plasma. In another embodiment, the plasma is human plasma. Although not wishing to be bound by any particular scientific theory, it is believed that the administration of blood substitutes may dilute the concentration of coagulation factors to an undesirable level. Accordingly, using plasma as the diluent for the oxygen carrying component avoids this problem. Plasma can be collected by any means known in the art, provided that red cells, white cells and platelets are essentially removed. Preferably, it is obtained using an automated plasmaphoresis apparatus. Plasmaphoresis apparatuses are commercially available and include, for example, apparatuses that separate plasma from the blood by ultrafiltration or by centrifugation. An ultrafiltration-based plasmaphoresis apparatus such as manufactured by Auto C, A200 (Baxter International Inc., Deerfield, Ill.) is suitable because it effectively removes red cells, white cells and platelets while preserving coagulation factors.

Plasma may be collected with an anticoagulant, many of which are well known in the art. Preferred anti-coagulants are those that chelate calcium such as citrate. In one embodiment, sodium citrate is used as an anticoagulant at a final concentration of 0.2-0.5%, preferably 0.3-0.4%, and most preferably at 0.38%. It may be used in a range from The plasma may be fresh, frozen, pooled and/or sterilized. While plasma from exogenous sources may be preferred, it is also within the present invention to use autologous plasma that is collected from the subject prior to formulation and administration of the resuscitation fluid.

In addition to plasma from natural sources, synthetic plasma may also be used. The term "synthetic plasma," as used herein, refers to any aqueous solution that is at least isotonic and that further comprises at least one plasma protein.

Oncotic Agent

In one embodiment, the resuscitation fluid further contains an oncotic agent The oncotic agent is comprised of molecules whose size is sufficient to prevent their loss from circulation by traversing the fenestrations of the capillary bed into the interstitial spaces of the tissues of the body. Examples of oncotic agents include, but are not limited to, albumin such as human serum albumin, polysaccharides such as dextran, and polysaccharide derivatives such as hydroxymethyl alpha (1, 4) or (1, 6) polymers, Herastarch® (McGaw, Inc.) and cyclodextrins. In one embodiment, the oncotic agent is about 5% (w/v) albumin. In another embodiment, the oncotic agent is a polysaccharide, such as Dextran, in a molecular weight range of 30,000 to 50,000 daltons (D). In yet another embodiment, the oncotic agent is a polysaccharide, such as Dextran, in a molecular weight range of 50,000 to 70,000 D. High molecular weight dextran solutions are more effective in preventing tissue swelling due to their lower rates of leakage from capillaries. In one embodiment, the concentration of the polysaccharide is sufficient to achieve (when taken together with chloride salts of sodium, calcium and magnesium, organic ion from the organic salt of sodium and hexose sugar discussed above) colloid osmotic pressure approximating that of normal human serum, about 28 mm Hg.

Crystalloid Agent

The resuscitation fluid may also comprise a crystalloid agent. The crystalloid agent can be any crystalloid which, in the form of the resuscitation fluid composition, is preferably capable of achieving an osmolarity greater than 800 mOsm/l, i.e. it makes the resuscitation fluid "hypertonic". Examples of suitable crystalloids and their concentrations in the resuscitation fluid include, but are not limited to, 3% w/v NaCl, 7% NaCl, 7.5% NaCl, and 7.5% NaCl in 6% w/v dextran. In one embodiment, the resuscitation fluid has an osmolarity of between 800 and 2400 mOsm/l.

When the resuscitation fluid further comprises a crystalloid and is hypertonic, the resuscitation fluid may provide improved functionality for rapid recovery of hemodynamic parameters over other blood substitute compositions, which include a colloid component. Small volume highly hypertonic crystalloid infusion (e.g., 1-10 ml/kg) provides significant benefits in the rapid and sustained recovery of acceptable hemodynamic parameters in controlled hemorrhage. (See, e.g., Przybelski, R. J., E. K. Daily, and M. L. Birnbaum, "The pressor effect of hemoglobin—good or bad?" In Winslow, R. M., K. D. Vandegriff, and M. Intaglietta, eds. Advances in Blood Substitutes. Industrial Opportunities and Medical Challenges. Boston, Birkhauser (1997), 71-85). In another embodiment, the lipid emulsion used is Intralipid®. In another embodiment, the lipid emulsion used is 20% Intralipid®. In one embodiment, the lipid comprises anti-inflammatory lipids such as omega-3 fatty acids.

Ion Concentrations

In one embodiment, the resuscitation fluid of the present invention includes a concentration of calcium, sodium, magnesium and potassium ion which is within the range of normal physiological concentrations of said ions in plasma. In general, the desired concentration of these ions is obtained from the dissolved chloride salts of calcium, sodium and magnesium. The sodium ions may also come from a dissolved organic salt of sodium that is also in solution.

In one embodiment, the sodium ion concentration is in a range from 70 mM to about 160 mM. In another embodiment, the sodium ion concentration is in a range of about 130 to 150 mM.

In one embodiment, the concentration of calcium ion is in a range of about 0.5 mM to 4.0 mM. In another embodiment, the concentration of calcium ion is in a range of about 2.0 mM to 2.5 mM.

In one embodiment, the concentration of magnesium ion is in a range of 0 to 10 mM. In another embodiment, the concentration of magnesium ion is in a range of about 0.3 mM to 0.45 mM. It is best not to include excessive amounts of magnesium ion in the resuscitation fluid of the invention because high magnesium ion concentrations negatively affect the strength of cardiac contractile activity. In a preferred embodiment of the invention, the solution contains subphysiological amounts of magnesium ion.

In one embodiment, the concentration of potassium ion is in a subphysiological range of between 0-5 mEq/l $K^+$ (0-5 mM), preferably 2-3 mEq/l $K^+$ (2-3 mM). Thus, the resuscitation fluid allows for dilution of the potassium ion concentration in stored transfused blood. As a result, high concentrations of potassium ion and potential cardiac arrhythmias and cardiac insufficiency caused thereby can be more easily controlled. The resuscitation fluid containing a subphysiological amount of potassium is also useful for purposes of blood substitution and low temperature maintenance of a subject.

In one embodiment, the concentration of chloride ion is in the range of 70 mM to 160 mM. In another embodiment, the concentration of chloride ion is in the range of 110 mM to 125 mM.

Carbohydrates

The resuscitation fluid may also contain a carbohydrate or a mixture of carbohydrates. Suitable carbohydrates include, but are not limited to, simple hexose (e.g., glucose, fructose and galactose), mannitol, sorbitol or others known to the art. In one embodiment, the resuscitation fluid includes physiological levels of a hexose. "Physiological levels of a hexose" includes a hexose concentration of between 2 mM to 50 mM. In one embodiment, the resuscitation fluid contains 5 mM glucose. At times, it is desirable to increase the concentration of hexose in order to lower fluid retention in the tissues of a subject. Thus the range of hexose may be expanded up to about 50 mM if necessary to prevent or limit edema in the subject under treatment.

Buffering Agent

The resuscitation fluid of the present invention may further comprise a biological buffer to maintain the pH of the fluid at the physiological range of pH7-8. Examples of biological buffers include, but are not limited to, N-2-Hydroxyethylpiperazine-N'-2-hydroxypropanesulfonic acid (HEPES), 3-(N-Morpholino)propanesulfonic acid (MOPS), 2-([2-Hydroxy-1,1-bis(hydroxymethyl)ethyl]amino) ethanesulfonic acid (TES), 3-[N-tris(Hydroxy-methyl)methylamino]-2-hydroxyethyl]-1-piperazinep ropanesulfonic acid (EPPS), Tris [hydrolymethyl]-aminoethane (THAM), and Tris [Hydroxylmethyl]methyl aminomethane (TRIS).

In one embodiment, the buffering agent is histidine, imidazole, substituted histidine or imidazole compounds retaining the amphoteric site of the imidazole ring, oligopeptides containing histidine, or mixtures thereof. Histidine is also capable of reducing reactive oxygen species (see e.g., Simpkins et al., J. Trauma. 2007, 63:565-572). Histidine or imidazole is typically used in a concentration range of about 0.01M to 0.5M.

In another embodiment, the resuscitation fluid of the present invention uses normal biological components to maintain in vivo biological pH. Briefly, some biological compounds, such as lactate, are capable of being metabolized in vivo and act with other biological components to maintain a biologically appropriate pH in an animal. The biological components are effective in maintaining a biologically appropriate pH even at hypothermic temperatures and at essentially bloodless conditions. Examples of the normal biological components include, but are not limited to carboxylic acids, salt and ester thereof. Carboxylic acids have the general structural formula of RCOOX, where R is an alkyl, alkenyl, or aryl, branched or straight chained, containing 1 to 30 carbons which carbons may be substituted, and X is hydrogen or sodium or other biologically compatible ion substituent which can attach at the oxygen position, or is a short straight or branched chain alkyl containing 1-4 carbons, e.g., $—CH_3$, $—CH_2\ CH_3$. Examples of carboxylic acids and carboxylic acid salts include, but are not limited to, lactate and sodium lactate, citrate and sodium citrate, gluconate and sodium gluconate, pyruvate and sodium pyruvate, succinate and sodium succinate, and acetate and sodium acetate.

Other Components

In addition to the components discussed above, the resuscitation fluid may further comprise other additives such as antibiotics, vitamins, amino acids, vessel expanders such as alcohols and polyalcohols, surfactants, and antibodies against harmful cytokines such as tumor necrosis factor (TNF) or interleukins. In addition, other gases, such as hydrogen sulfide which is a regulator of blood pressure, or carbon monoxide which has cytoprotective properties that can be used to prevent the development of pathologic conditions such as ischemia reperfusion injury, may be added.

Preparation of the Resuscitation Fluid

The resuscitation fluid may be prepared by mixing the lipid component, the aqueous carrier, and any other components to form an emulsion. Commonly used mixing methods include, but are not limited to, stirring, shaking, vibration and sonication. In one embodiment, the resuscitation fluid is formed by mixing a pre-formed lipid emulsion, such as Intralipid®, with the aqueous carrier and other components.

In order to increase the oxygen content in the resuscitation fluid, the resuscitation fluid may be oxygenated by bubbling pure oxygen or a gas with an oxygen content in the range of 21% to 100% (v/v), preferably 40% to 100% (v/v), more preferably 60% to 100% (v/v), and most preferably 80% to 100% (v/v), through the resuscitation fluid for a period of 30 seconds or longer, preferably 1-15 minutes, more preferably 1-5 minutes. The oxygenation time for a resuscitation fluid of a particular composition may be determined experimentally. In one embodiment, the resuscitation fluid is oxygenated immediately prior to application.

In one embodiment, the resuscitation fluid comprises an oxygenated lipid emulsion. As used herein, the term "oxygenated lipid emulsion' or "oxygenated resuscitation fluid" refers to a specific type of gassed lipid emulsion or gassed resuscitation fluid which has been forced to absorb oxygen such that the total concentration of oxygen contained therein is greater than that present in the same liquid at atmospheric equilibrium conditions.

Kits

Another aspect of the present invention relates to a resuscitation kit. In one embodiment, the resuscitation kit comprises an oxygenated resuscitation fluid and at least one additive. Examples of additives include, but are not limited to, oncotic agent, crystalloid agent, vessel expander, cardioplegic, or cardiotonic agent scavengers of free radicals or mediators, cell signaling modulators, and receptor agonists or antagonists. In another experiment, the kit further contains an intravenous infusion (IV) set. In another embodiment, the oxygenated resuscitation fluid is contained in one or more preloaded syringes for emergency application. In another embodiment, the kit further contains an oxygen container that can be used to re-oxygenate the resuscitation fluid immediately prior to application. The oxygen container may contain pure oxygen, or a gas mixture of oxygen with either hydrogen sulfide or carbon monoxide or both. In another embodiment, the kit contains a resuscitation fluid, and an air pump for oxygenating the resuscitation fluid with ambient air immediately prior to application.

Treatment Methods

Another aspect of the present invention relates to a method for treating conditions related to lack of blood supply with a lipid-based resuscitation fluid. Conditions related to a lack of blood supply include, but are not limited to, hypovolemia, ischemia, hemodilution, trauma, septic shock, cancer, anemia, cardioplegia, hypoxia and organ perfusion. The term "hypovolemia," as used herein, refers to an abnormally decreased volume of circulating fluid (blood or plasma) in the body. This condition may result from "hemorrhage," or the escape of blood from the vessels. The term "ischemia," as used herein, refers to a deficiency of blood in a part of the body, usually caused by a functional constriction or actual obstruction of a blood vessel.

The resuscitation fluid may be administered intravenously or intraarterially to a subject in need of such treatment. Administration of the resuscitation fluid can occur for a period of seconds to hours depending on the purpose of the resuscitation fluid usage. For example, when used as a blood volume expander and an oxygen carrier for the treatment of severe hemorrhage shock, the usual time course of administration is as rapidly as possible, which may range from about 1 ml/kg/hour to about 15 ml/kg/min.

When used for organ perfusion during an organ transplantation, the resuscitation fluid may be administered slowly over a period of hours.

While the resuscitation fluid of the present invention is being administered to and circulated through the subject, various agents such as cardioplegic or cardiotonic agents may be administered either directly into the subject's circulatory system, administered directly to the subject's myocardium, or added to the resuscitation fluid of the present invention. These components are added to achieve desired physiological effects such as maintaining regular cardiac contractile activity, stopping cardiac fibrillation or completely inhibiting contractile activity of the myocardium or heart muscle.

Cardioplegic agents are materials that cause myocardial contraction to cease and include anesthetics such as lidocaine, procaine and novocaine and monovalent cations such as potassium ion in concentrations sufficient to achieve myocardial contractile inhibition. Concentrations of potassium ion sufficient to achieve this effect are generally in excess of 15 mM.

During revival of a subject, the subject may be re-infused with a mixture of the resuscitation fluid described along with blood retained from the subject or obtained from blood donors. Whole blood is infused until the subject achieves an acceptable hematocrit, generally exceeding hematocrits of about 30%. When an acceptable hematocrit is achieved, perfusion is discontinued and the subject is revived after closure of surgical wounds using conventional procedures.

Another aspect of the present invention relates to a method of preserving the biological integrity of organs of a mammalian donor organism using the resuscitation fluid described. In one embodiment, the subject organ is chilled and the resuscitation fluid is perfused into the subject organ using a pumped circulating device such as a centrifugal pump, roller pump, peristaltic pump or other known and available circulatory pump. The circulating device is connected to the subject organ via cannulae inserted surgically into appropriate veins and arteries. When the resuscitation fluid is administered to a chilled subject organ, it is generally administered via an arterial cannula and removed from the subject via a venous cannula and discarded or stored.

EXAMPLES

The following example is put forth so as to provide those of ordinary skill in the art with a complete disclosure and description of how to carry out the method of the present invention and is not intended to limit the scope of the invention. Efforts have been made to ensure accuracy with respect to numbers used (e.g., amounts, temperature, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

Methods and Materials

Lipid emulsion: 20% Intralipid (marketed and sold by Baxter International Inc., Deerfield, Ill.) was used as a model lipid emulsion. It is composed of 20% soy bean oil, 1.2% egg yolk phospholipids 2.25% glycerin, water and sodium hydroxide to adjust the pH to 8.

Determination of oxygen content of Intralipid: Samples of distilled water, Ringer's lactate (RL) and Intralipid (20%) (1 ml each) were left open to air in 2.0 ml tubes for 30 minutes prior to dissolved gas analysis. Volumes of 50 uL drawn from each of these fluids were injected into a Sievers purge vessel at 37° C. containing 36 ml of a mildly acidic solution consisting of 32 ml of 1M HCL and 4 ml of 0.5M ascorbic acid. The solution was continuously purged with high purity helium to transport any oxygen released from the samples to a mass spectrometer (HP 5975) for direct gas analysis. Signals generated at m/z=32 upon injection of RL and lipid emulsion samples were integrated using Peakfit and compared to those obtained with distilled water.

Animals and animal procedures: Male and female mice weighing 27-47 grams were utilized. The strains were either CD-1 or NFR2. All comparisons utilized the same strain. Mice were anesthetized using ketamine/xylazine anesthesia administered subcutaneously. In order to prevent the skewing of data due to the cardiodepressant effects of the anesthetic agent, the experiment was aborted and the mouse euthanized in the rare instance when more anesthetic was required than the calculated dose. Once it was clear that the mouse was well-anesthetized, the carotid artery was cannulated. As much blood as possible was removed in one minute. This resulted in the loss of 55% of blood volume and 100% lethality without any infusion. Immediately after blood removal infusions were administered over one minute.

Either RL or Intralipid was administered at a volume equal to the amount of blood that had been removed. Blood pressure was measured at the carotid artery using a BP-2 monitor made by Columbus Instruments (Columbus, Ohio). This monitor measures the blood pressure as a voltage. A standard curve was prepared. Measured voltages were converted to blood pressure (BP) using the following formula:

BP=[Voltage−0.1006]/0.0107

No warming measures were applied to the mice. No measures were taken to support respiration.

Statistical Analysis: Data were analyzed using Student's unpaired t test.

Example 2

Oxygen Content of the Resuscitation Fluid

Intralipid® 20% I.V. Fat Emulsion (marketed and sold by Baxter International Inc., Deerfield, Ill.) was used as a sample resuscitation fluid (RF). The composition of Intralipid® is 20% soybean oil, 1.2% egg yolk phospholipids, 2.25% glycerin, water and sodium hydroxide to adjust the pH to 8. Oxygen content in the RF was measured using mass spectrometry. As shown in Table I, the oxygen content of the RF was nearly twice that of Ringer's lactate (RL), a standard resuscitation fluid infused when a large amount of blood is lost. The oxygen content of RL was equivalent to that of water. As shown in Table II, the oxygen content of the RF was increased five-fold by bubbling oxygen through it for approximately 1 minute. After oxygen loading, the oxygen content of RF compared favorably to that of blood with the minimum acceptable hemoglobin level (i.e., 7.0 g/dl). Table III shows that theoretical oxygen content in RF with higher lipid contents.

TABLE I

Oxygen content of Ringer's lactate and Intralipid ® 20%

| | Ringer's lactate | Intralipid ® 20% |
|---|---|---|
| Oxygen Content* | 0.91 ± 0.11* | 1.78 ± 0.09* |

*the oxygen content is expressed as the amount relative to the oxygen content in water.

TABLE II

Oxygen solubility in various liquids at 1 atm
Oxygen Content at 25° C. and Sea level Pressure

| Blood (hemoglobin of 7.0) | 72.8 mg/L |
|---|---|
| Water | 8.3 mg/L |
| LM (20%) | 15.1 mg/L |
| LM (20% after oxygen perfusion) | 75.5 mg/L |

TABLE III

Theoretical oxygen content in RF with higher lipid concentrations
Theoretical oxygen content at higher concentrations

| LM (40%) | 24.9 mg/L |
|---|---|
| LM (40% after oxygen perfusion) | 124.5 mg/L |
| LM (60%) | 33.2 mg/L |
| LM (60% after oxygen perfusion) | 166.0 mg/L |

Example 3

The Effect of Resuscitation Fluid in Restoring Arterial Pressure in Mice with Severe Hemorrhagic Shock The effect of the RF in Example 2 on blood pressure was determined in mice. Mice were anesthetized and a cannula was placed into the carotid artery. All the blood that could be removed was removed via the carotid artery. After the blood was removed a volume of either RL or RF was given equal to the amount of blood removed. 6 mice were in the RF group and 6 mice were in the RL group. The observation period was one hour. Two of the mice given RL died within ten minutes. All mice given RF lived through the entire hour observation period and until euthanized at 1-4 hours. Animals were euthanized whenever they began to awaken from the anesthesia or at the end of the observation period to prevent suffering.

Figure 2:
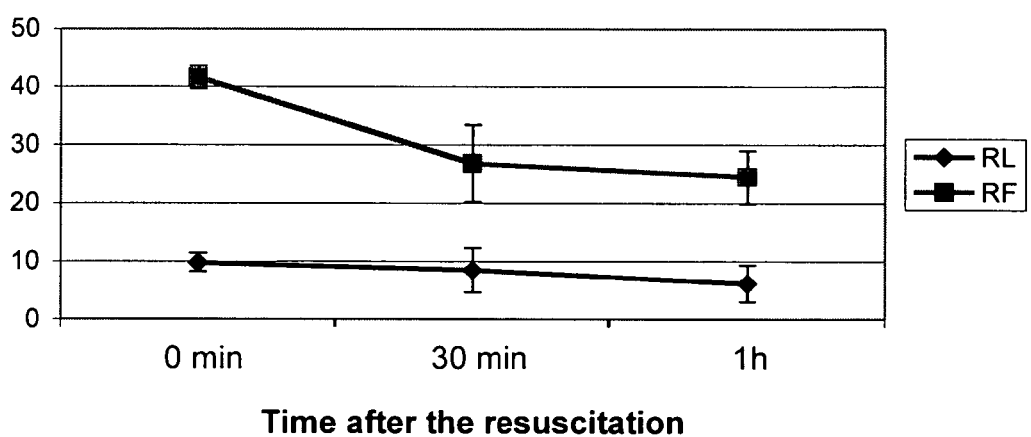
FIG. 2 is a diagram showing diastolic blood pressure in mice treated with different resuscitation fluids after severe hemorrhagic shock.

FIGS. 1 and 2 show the difference between the systolic blood pressure (FIG. 1) and diastolic blood pressure (FIG. 2) after hemorrhage and after infusion of RL or RF at time=0, 30 and 60 minutes. The Y axis represents the blood pressure attained after infusion minus the blood pressure after hemorrhage in mm of Hg. The X axis shows the specific time after the infusion. All data were analyzed for statistical significance using an unpaired two tailed t test. These graphs show that RF raised the blood pressure higher than RL.

Figure 3:
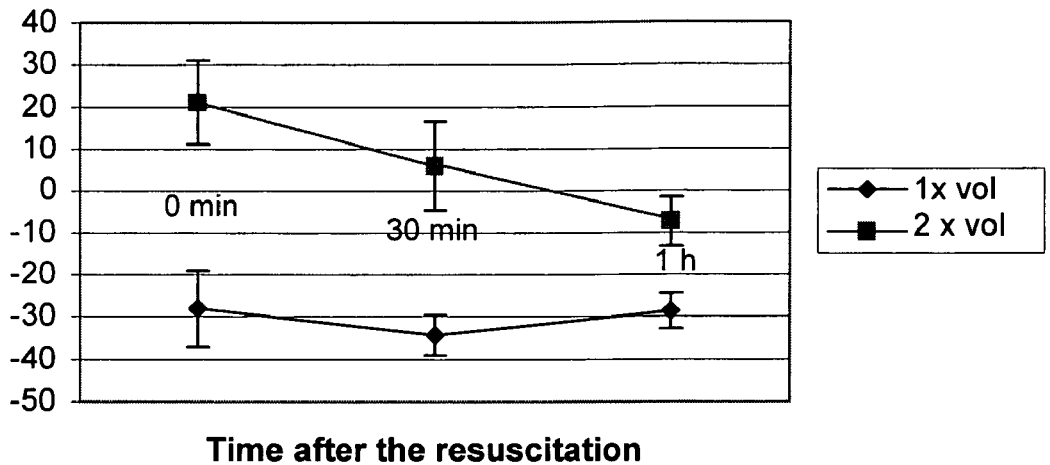
FIG. 3 is a diagram showing systolic blood pressure in mice treated with a resuscitation fluid of different volumes after severe hemorrhagic shock.
Figure 4:
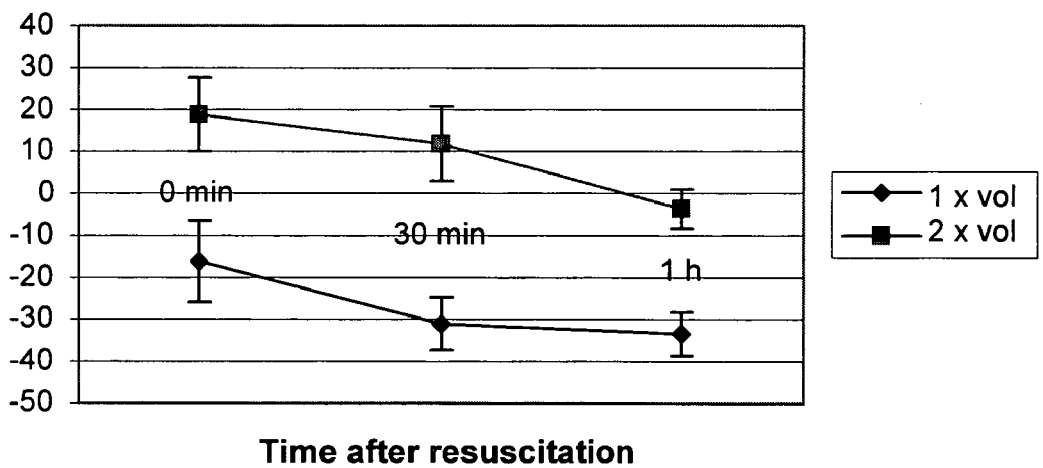
FIG. 4 is a diagram showing diastolic blood pressure in mice treated with a resuscitation fluid of different volumes after severe hemorrhagic shock.

In another experiment, RF at a volume twice the amount of blood removed was given. This led to an even greater increase in the blood pressure as shown in FIGS. 3 and 4. The points on the graph represent the mean of 6 mice +/−SE. The Y-axis shows the difference between the systolic blood pressure (FIG. 3) and diastolic blood pressure (FIG. 4) after infusion of RF at 1× the blood volume (diamond) or 2× the blood volume (square) minus the baseline pressure prior to hemorrhage in mm of Hg. Under this scheme therefore, 0 represents the blood pressure at the beginning of the experiment before hemorrhage. The X axis shows specific times after the infusion. 2× the blood volume raised the blood pressure higher than the pressure reached after infusion of 1× the blood volume ($p<0.01$). Moreover, the pressure achieved after infusion of 2× the removed blood volume exceeded the pressure that existed prior to hemorrhage.

Figure 5:
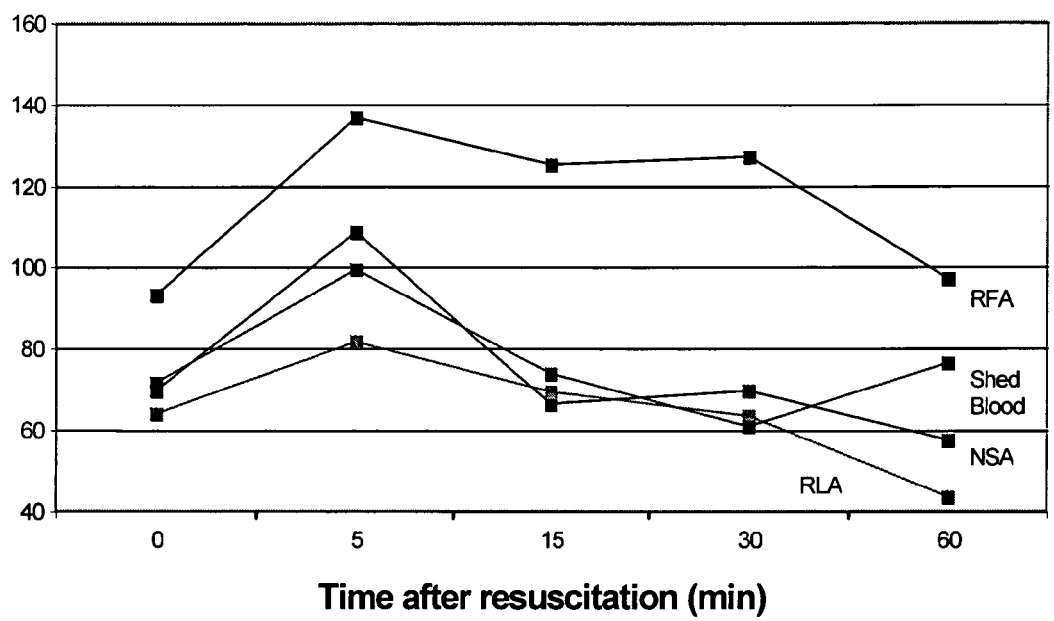
FIG. 5 is a diagram showing a percentage of systolic blood pressure in mice treated with albumin-containing resuscitation fluids and mice treated with shed blood after severe hemorrhagic shock.

In another experiment, a resuscitation fluid containing Intralipid® 20% and 5% (w/v) albumin was prepared by dissolving albumin (Sigma Aldrich, 99% pure, fatty acid free, essentially globulin free, catalog number A3782-5G) in Intralipid® 20% to a final concentration of 50 mg/ml. The new resuscitation fluid with albumin (RFA) was tested using the experimental procedure described above. Albumin dissolved in normal saline (NSA) and Ringer's lactate (RLA) at 50 mg/ml, as well as the shed blood (i.e., the blood that had been removed from the mice), were used as controls. In FIG. 5, the Y axis shows the percentage of the systolic blood pressure prior to hemorrhage achieved by infusion of the various fluids. The X axis shows specific times after the infusion. The data show that RFA is superior even to shed blood in maintaining blood pressure. Similar results were also obtained for the diastolic blood pressure (not shown). For each time point, an average of 6-7 mice is plotted. Differences between shed blood and RFA was statistically significant ($P<0.05$) at 5, 15 and 30 minutes.

These experimental results are consistent with the fact that the lipid micelles in the resuscitation fluid are capable of exerting an osmotic force and absorbing mediators of vascular potency, such as prostaglandins, nitric oxide, leukotrienes, and platelet activating factors.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

What is claimed is:

1. A method for treating hemorrhagic shock in a human or animal subject, comprising:
    administering to said subject an effective amount of a lipid based resuscitation fluid comprising a lipid component and an aqueous carrier, wherein said lipid component forms an emulsion with said aqueous carrier in the form of lipid micelles with a polar outer surface and an inner hydrophobic space.

2. The method of claim 1, wherein said hemorrhagic shock is severe hemorrhagic shock.

3. The method of claim 1, wherein said resuscitation fluid further comprises a plasma component.

4. The method of claim 3, wherein said plasma component is albumin.

5. The method of claim 4, wherein said albumin has a final concentration of approximately 5% (w/v).

6. The method of claim 1, wherein said resuscitation fluid further comprises at least one additive selected from the group consisting of oncotic agents, crystalloid agents, buffering agents, carbohydrates, salts, vitamins, antibodies, and surfactants.

7. The method of claim 1, wherein said resuscitation fluid further comprises a buffering agent.

8. The method of claim 7, wherein said buffering agent comprises histidine at a concentration of between 0.01M to 0.2M.

9. The method of claim 1, further comprising:
    oxygenating the lipid based resuscitation fluid prior to administration to said subject.

10. The method of claim 9, wherein said lipid based resuscitation fluid is oxygenated by bubbling an oxygen-containing gas through the lipid based resuscitation fluid for 1 to 5 minutes.

11. The method of claim 9, wherein said lipid based resuscitation fluid is oxygenated by bubbling a gas comprising 90%-100% (v/v) oxygen through the lipid based resuscitation fluid for about 1 minute.

12. The method of claim 1, wherein said resuscitation fluid is administered either intravenously or intra-arterially.

13. The method of claim 1, wherein said resuscitation fluid is prepared by mixing said lipid component with said aqueous carrier to form said emulsion.

14. A method for treating hemorrhagic shock in a human or animal subject, comprising:
    administering to said subject an effective amount of a lipid based resuscitation fluid consisting essentially of:
    a lipid component;
    a polar liquid carrier; and
    at least one additive selected from the group consisting of oncotic agents, crystalloid agents, buffering agents, carbohydrates, salts, vitamins, amino acids, vessel expanders, antibodies, and surfactants,
    wherein said lipid component forms an emulsion with said a polar liquid carrier in the form of lipid micelles with a polar outer surface and an inner hydrophobic space.

15. The method of claim 14, wherein said hemorrhagic shock is severe hemorrhagic shock.

16. A method for treating hemorrhagic shock in a human or animal subject, comprising:
    administering to said subject an effective amount of a lipid based resuscitation fluid comprising a lipid component and an aqueous carrier,
    wherein said lipid component forms an emulsion with said aqueous carrier in the form of lipid micelles with a polar outer surface and an inner hydrophobic space and wherein said emulsion is administered into said subject without further encapsulation.

17. The method of claim 16, wherein said hemorrhagic shock is severe hemorrhagic shock.

* * * * *